United States Patent [19]

Sesin

[11] Patent Number: 4,845,085
[45] Date of Patent: Jul. 4, 1989

[54] ANTIFUNGAL AGENT

[75] Inventor: David F. Sesin, Westfield, N.J.

[73] Assignee: Merck & Co., Inc., Rahway, N.J.

[21] Appl. No.: 230,283

[22] Filed: Aug. 9, 1988

[51] Int. Cl.$^4$ .................. A61K 31/395; C07D 273/08
[52] U.S. Cl. ..................................... 514/183; 540/454
[58] Field of Search ......................... 540/454; 314/183

[56] References Cited
U.S. PATENT DOCUMENTS
4,341,533 2/1983 Akimoto et al. .

OTHER PUBLICATIONS
Kupchan, S. M. et al., J. Am. Chem. Soc. 94:4, 1354 (1972).

Primary Examiner—Robert T. Bond
Attorney, Agent, or Firm—Alice O. Robertson; Michael C. Sudol

[57] ABSTRACT

A novel semi-synthetic compound, 10-[(3-chloro-4-methoxyphenylmethyl]-6-methyl-3-(2-methylpropyl)-16-(1-methyl-3-phenyl-2-propenyl)-1,4-dioxa-8, 11-diazacyclohexadec-13-ene-2,5,9,12-tetrone, which has potential as a treating agent for mycotic infections is disclosed.

3 Claims, No Drawings

ANTIFUNGAL AGENT

DESCRIPTION OF THE INVENTION

The present invention is directed to a new semi-synthetic compound represented by the formula:

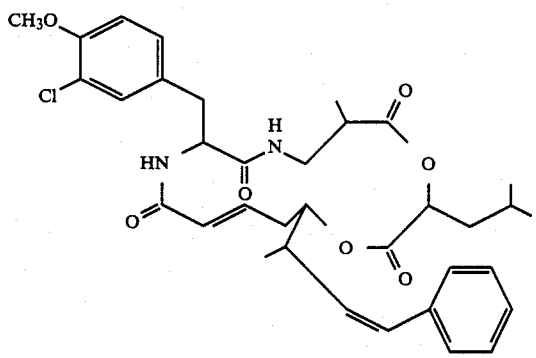

The compound may also be identified by the chemical name, 10-[(3-chloro -4-methoxyphenyl)methyl]-6-methyl-3-(2-methylpropyl)-16-(1-methyl-3-phenyl-2-propenyl)-1,4-dioxa-8,11-diazacyclohexadec-13-ene-2,5,9,12-tetrone. For convenience, the compound hereinafter shall be referred to as Compound I.

Compound I has a molecular weight of 638, is of high solubility in organic solvents and adaptable to be employed in solution. It is also adaptable to be employed in aqueous dispersions.

Compound I may be produced from an antibiotic compound identifiable by the Chemical Abstracts nomenclature of 10-[(3-chloro-4-methoxy-phenyl)methyl]-6-methyl-3-(2 methylpropyl)-16-[1-(3-phenyloxiranyl)ethyl]-1,4-dioxa-8,11-diaza cyclohexadec-13-ene-2,5,9,12-tetrone (Compound A) having the structure

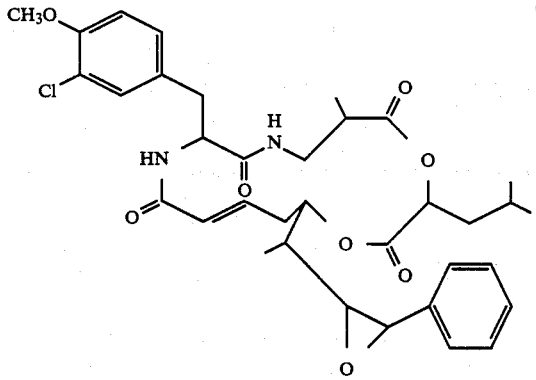

disclosed and claimed in copending application Ser. No. 219942 in the name of Hirsch et al., and produced by cultivating an unidentified strain of Nostoc sp., ATCC 53789.

Compound I may be prepared by treating Compound A with a zinc-copper couple or with diphosphorus tetraiodide ($P_2I_4$) in ether solution with pyridine or like base as catalyst.

Suitable zinc-copper couple for the reaction may be made by methods described in the literature just prior to use. One method is to stir zinc dust and 3% hydrochloric acid, then washing successively with 3% hydrochloric acid, with distilled water, with 2% copper sulfate, with distilled water, with absolute ethanol, followed by absolute ether, then drying over $P_2O_5$.

Zinc-copper couple also may be obtained by heating a mixture of cupric oxide and zinc dust in a stream of hydrogen nitrogen at 500° C.

These and other methods for preparing zinc-copper couple may be found described in Fieser & Fieser, "Reagents for Organic Synthesis" pp 1292-1293, John Wiley & Sons, Inc. New York and references cited therein.

Diphosphorus tetraiodide may be prepared by the reaction of phosphorus trichloride and potassium iodide under anhydrous conditions as described by H. Suzuki et al, Synthesis, 12, 905-908 (1978).

In such method, phosphorus trichloride is added dropwise with the exclusion of moisture to a stirred suspension of potassium iodide. After completion of the addition, the mixture is heated for several hours under reflux. The solvent thereafter removed under reduced pressure and the residue allowed to crystallize from 1,2 dichloroethane.

The exact amount of the reducing agent is not critical but generally an amount equivalent to that of starting Compound A is preferred.

A solvent is employed as reaction medium. When zinc-copper couple is the reagent, the solvent is ethanol or a lower alkanol. When the reducing agent is diphosphorus tetraiodide, the preferred solvent is ether to which a catalytic amount of pyridine or like heteroaromatic base has been added.

In carrying out the zinc-copper couple reduction, Compound A, zinc-copper couple and ethanol or other alkanol solvent are stirred together under reflux until the reaction is complete. Completion of the reaction may be monitored for the disappearance of Compound A by a reverse phase high performance liquid chromatographic (HPLC) column (such as Zorbax from Dupont; of siliceous microparticulate porous particles; 4.6 mm×25 cm) and using acetonitrile/water as eluant, preferably at a ratio of 60/40. Upon completion of the reaction, the reaction mixture is filtered to remove metal oxides, and the volatiles removed from the filtrate by subjecting the filtrate to reduced pressure and to obtain a residue. The residue is then chromatographed on a reverse phase HPLC column using acetonitrile/water, preferably 70/30, as eluant and the eluate subjected to reduced pressure to vaporize the volatiles and to obtain the desired Compound I.

In carrying out the reaction with diphosphorus tetraiodide, an ethereal solution of diphosphorus tetraiodide is added with stirring to a solution of Compound A in modified pyridine, i.e., pyridine to which about 1% dry ether has been added. After completion of the addition, stirring is continued at ambient temperature for about 3 to 6 hours. At the end of this period, the reaction is quenched by the addition of water and the aqueous solution extracted with ether. The ether solution is washed succcessively with dilute acid, such as IN hydrochloric acid, then with 5% hydrogen sulfite and brine. The washed ether solution is dried and the crude product recovered therefrom by vaporizing off the solvent in a conventional manner. The product residue may be purified by chromatographing on a reverse phase column. A 70/30 acetonitrile/water mixture is a preferred eluting agent. Other eluting agents include 90/10 methanol/water.

Compound I is adapted to be employed for the control of fungal organisms, particularly the same organisms that are controlled by Compound A, such as Cryptococcus species among the yeast organisms and various filamentous fungi. Filamentous fungi include Aspergillus species, Penicillium species, Phoma species, *Alternaria solani, Cochliobolus miyabeanus, Botrytis allii, Ceratocystis ulmi, Fusarium oxysporum* and the like.

The antifungal properties are most effectively utilized when Compound I is formulated into antifungal treating compositions with a biologically inert carrier which in cases of use in pharmaceutical applications should also be pharmaceutically acceptable.

The novel compositions are formulated according to conventional compounding techniques with a biologically inert carrier, generally with the aid of a surface active dispersing agent. The compositions may contain 5% or more by weight of the active compound and, if a concentrate composition, may contain 15% or more. In preparing the compositions, Compound I is intimately admixed with an appropriate carrier.

Suitable carriers include liquids such as water, glycol, oil, alcohols and the like which may include buffering agents, sodium chloride, dextrose and various suspending, stabilizing, solubilizing or dispersing agents. Solid carriers include starches, sugars, kaolin, ethyl cellulose, calcium carbonate, sodium carbonate, calcium phosphate, talc, lactose, and for tablets, lubricants such as calcium or magnesium stearate, binders, disintegrating agents and the like.

Compound I may also be formulated in creams and ointments such as white petrolatum, anhydrous lanolin, cetyl alcohol, cold cream, glyceryl monostearate, rose water and the like.

The antifungal compositions may be employed by applying to the area where fungal control is desired in such amounts as necessary to effect the desired control.

The following examples illustrate the invention but are not to be construed as limiting:

EXAMPLE I 50 milligrams (0.08 millimole) of Compound A is intimately admixed with zinc-copper couple (prepared from 850 milligrams of zinc dust and 10 milliliters of 2 percent copper sulfate solution) and 8 milliliters of ethanol, and the resulting mixture held at reflux temperature while the progress of the reaction is monitored for the disappearance of Compound A by HPLC (reverse phase, Zorbax 4.6 mm×25 cm) using 60/40 acetonitrile/water. On completion of the reaction, the reaction mixture is filtered and the volatiles removed from the filtrate in vacuo to recover an oil. The oil is then chromatographed on a reverse phase column (Zorbax, 21.2 mm×25 cm) using 70/30 acetonitrile/water as eluting agent, and the eluate evaporated to dryness to recover purified Compound I.

EXAMPLE II

A solution of 45 milligrams (0.08 millimole) phosphorus tetraiodide ($P_2I_4$) in 5 milliliters of dry ether is added with stirring to a solution of 50 milligrams (0.08 millimole) of Compound A in 5 milliliters of dry ether containing 500 microliters of pyridine. After completion of the addition, the reaction mixture is stirred at ambient temperature for four hours. At the end of this period, 20 milliliters of water is added to the mixture to quench the reaction and the aqueous solution extracted with ether. The ether fraction is washed successively with equal volumes of 1N hydrochloric acid, 5% hydrogen sulfite and brine. The ether layer is then dried with anhydrous sodium sulfate, and then the solvent removed in vacuo from the dried solution to obtain an oil which is chromatographed on a reverse phase column (Zorbax, 21.2 mm×25 cm) using 70/30 acetonitrile/water to obtain purified Compound I.

Starting Material

The starting material for the synthesis of Compound I is a natural product identifiable by formula A and which may be obtained by the cultivation of a cyanobacteria (Nostoc sp.) ATCC 53789 and isolating it from either a methanol extract of the cells or from the filtered (or supernatant) broth.

The cultivation may be carried out by inoculating a tube of Nostoc sp. culture ATCC 53789 in BG-13 medium and the inoculated culture incubated at 25° C. under a continuously replenished atmosphere of 5 percent (v/v) carbon dioxide in air and under continuous illumination at 5000 lux. At the end of this period, the cells are transferred to a larger (2–10 fold) volume of medium and the medium similarly cultivated under an atmosphere of 5% carbon dioxide in air and under continuous illumination at 5000 lux for 12–20 days to obtain the compound of formula A. The latter may be extracted from the cells with methanol. Some of the desired compound also may be found in the fermentation broth and extracted with ethyl acetate. Compound A may be recovered from the methanol extract by partitioning with methylene chloride and vaporizing the volatiles or from the ethyl acetate extract of the broth by vaporizing the volatiles and thereafter chromatographing the residue to purify the residue employing 75/25 methanol/water as eluent.

BG-13 medium is of the following composition in grams per liter: $NaNO_3$, 1.5–3.0; $NaHCO_3$, 1.7; $K_2HPO_4$, 0.031–0.34; sulfate as $MgSO_4.7H_2O$, 0.075 or $Na_2SO_4$, 0.14; $CaCl_2.H_2O$, 0.036; citric acid, 0.006; ferric ammonium citrate, 0.006; EDTA ($Na_2Mg$ salt), 0.001; $Na_2CO_3$, 0.02; trace element mix, 1 ml; and distilled water to 1000 ml wherein the trace element mix prepared in 0.1 N HCl, is of the following contents in grams per liter: $H_3BO_3$, 2.86; $MnCl_2.4H_2O$, 1.81; $ZnSO_4.7H_2O$, 0.222; $Na_2MoO_4.2H_2O$, 0.390; $CuSO_4.5H_2O$, 0.079; $CoCl_2.6H_2O$, 0.040; and wherein the pH of the solution is 7.6.

The production of Compound A from Nostoc sp. is more fully described in the aformentioned application Ser. No. 219942 of Hirsch et al.

What is claimed is:

1. A compound of the formula:

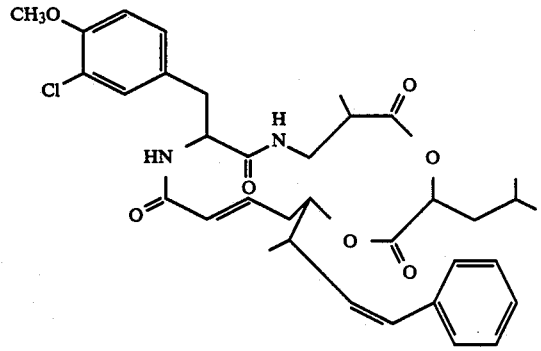

2. 10-[(3-Chloro-4-methoxyphenyl)methyl]-6-methyl-3-(2-methylpropyl)-16-(1-methyl-3-phenyl-2-propenyl)-1,4-dioxa-8,11-diazacyclohexadec-1,3-ene-2,5,9,12-tetrone.

3. An antifungal composition comprising from about 5 to about 15 percent by weight of a compound of claim 1 in admixture with a pharmaceutically acceptable carrier.

* * * * *

UNITED STATES PATENT AND TRADEMARK OFFICE
CERTIFICATE OF CORRECTION

PATENT NO. : 4,845,085

DATED : July 4, 1989

INVENTOR(S) : David F. Sesin

It is certified that error appears in the above-identified patent and that said Letters Patent is hereby corrected as shown below:

Col. 5, line 3, change "1,3-ene" to -- 13-ene --

Signed and Sealed this

Twenty-first Day of August, 1990

Attest:

HARRY F. MANBECK, JR.

*Attesting Officer*      *Commissioner of Patents and Trademarks*